US007880040B2

(12) United States Patent
Mukhopadhyay et al.

(10) Patent No.: US 7,880,040 B2
(45) Date of Patent: *Feb. 1, 2011

(54) METHOD FOR PRODUCING FLUORINATED ORGANIC COMPOUNDS

(75) Inventors: Sudip Mukhopadhyay, Williamsville, NY (US); Haridasan K. Nair, Williamsville, NY (US); Hsueh S. Tung, Getzville, NY (US); Michael Van Der Puy, Amherst, NY (US); Rajiv R. Singh, Getzville, NY (US); Haiyou Wang, Williamsville, NY (US); Robert C. Johnson, Lancaster, NY (US); Rajesh K. Dubey, Buffalo, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/592,442

(22) Filed: Nov. 3, 2006

(65) Prior Publication Data
US 2007/0129580 A1 Jun. 7, 2007

Related U.S. Application Data

(63) Continuation-in-part of application No. 11/118,504, filed on Apr. 29, 2005, application No. 11/592,442, which is a continuation-in-part of application No. 11/118,503, filed on Apr. 29, 2005, now Pat. No. 7,345,209, application No. 11/592,442, which is a continuation-in-part of application No. 11/118,530, filed on Apr. 29, 2005, now Pat. No. 7,189,884.

(60) Provisional application No. 60/763,086, filed on Jan. 27, 2006, provisional application No. 60/733,377, filed on Nov. 3, 2005, provisional application No. 60/567,428, filed on Apr. 29, 2004, provisional application No. 60/567,425, filed on Apr. 29, 2004, provisional application No. 60/567,427, filed on Apr. 29, 2004, provisional application No. 60/567,429, filed on Apr. 29, 2004, provisional application No. 60/567,426, filed on Apr. 29, 2004.

(51) Int. Cl.
C07C 19/08 (2006.01)
(52) U.S. Cl. .................................. 570/156; 570/136
(58) Field of Classification Search ........................ None
See application file for complete search history.

(56) References Cited

U.S. PATENT DOCUMENTS

| 2,931,840 A | 4/1960 | Marquis |
| 2,996,555 A | 8/1961 | Rausch et al. |
| 3,472,826 A | 10/1969 | Potts et al. |
| 3,659,023 A | 4/1972 | Regan |
| 4,086,407 A | 4/1978 | Fozzard |
| 4,798,818 A | 1/1989 | Baizer et al. |
| 4,900,874 A | 2/1990 | Ihara et al. |
| 5,162,594 A | 11/1992 | Krespan |
| 5,532,419 A | 7/1996 | Van Der Puy et al. |
| 5,545,777 A | 8/1996 | Morikawa et al. |
| 5,574,192 A | 11/1996 | Van Der Puy et al. |
| 5,679,875 A | 10/1997 | Aoyama et al. |
| 5,710,382 A | 1/1998 | Dunmead et al. |
| 5,969,198 A | 10/1999 | Thenappan et al. |
| 5,986,151 A | 11/1999 | Van Der Puy |
| 6,023,004 A | 2/2000 | Thenappan et al. |
| 6,031,141 A | 2/2000 | Malikarjuna et al. |
| 6,066,769 A | 5/2000 | Nappa et al. |
| 6,111,150 A | 8/2000 | Sakyu et al. |
| 6,369,284 B1 | 4/2002 | Nappa et al. |
| 6,548,719 B1 | 4/2003 | Nair et al. |
| 6,809,226 B1 | 10/2004 | Pennetreau et al. |
| 6,958,424 B1 | 10/2005 | Nair et al. |
| 6,977,316 B1 | 12/2005 | Mukhopadhyay et al. |
| 7,026,520 B1 | 4/2006 | Mukhopadhyay et al. |
| 7,026,521 B1 | 4/2006 | Mukhopadhyay et al. |
| 7,071,367 B1 | 7/2006 | Mukhopadhyay et al. |

(Continued)

FOREIGN PATENT DOCUMENTS

EP 0522639 1/1993

(Continued)

OTHER PUBLICATIONS

Haszeldine et al. "Free Radical additions to unsaturated systems" Journal of the Chemical Society, Section C: Organic Chemistry, Chemical Society, Letchworth, GB, vol. 3, 1970, pp. 414-421, XP002343900.
Database Beilstein, Beilstein Institute for Organic Chemistry, M. Van Der Puy. : J Fluorine Chemistry, vol. 81, No. 2, 1997, pp. 187-192, XP002424669.
Database Beilstein, Beilstein Institute for Organic Chemistry, Haszeldine, Steele: J. Chem. Soc., 1953, p. 1592, 1597, XP0022424670.

(Continued)

*Primary Examiner*—Daniel M Sullivan
*Assistant Examiner*—Yevegeny Valenrod
(74) *Attorney, Agent, or Firm*—Bruce O. Bradford

(57) ABSTRACT

Disclosed is a method for producing fluorinated organic compounds, including hydrofluoropropenes, which preferably comprises converting at least one compound of formula (I):

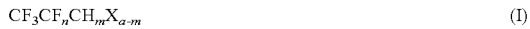

to at least one compound of formula (II)

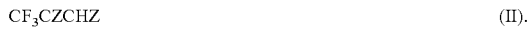

where each X is independently Cl, I or Br; each Z is independently H or F; n is 1 or 2; m is 1, 2 or 3, provided that when n is 1, m is 1 or 2; a is 2 or 3, and $a-m \geq 0$. Certain embodiments include the step of reacting fluorinated C2 olefin, such as tetrafluoroethylene, with a C1 addition agent under conditions effective to produce a compound of formula (I).

23 Claims, No Drawings

U.S. PATENT DOCUMENTS

| | | |
|---|---|---|
| 7,091,388 B2 * | 8/2006 | Tung et al. .............. 570/155 |
| 7,132,578 B1 | 11/2006 | Mukhopadhyay et al. |
| 7,135,601 B2 | 11/2006 | Mukhopadhyay et al. |
| 7,189,884 B2 | 3/2007 | Mukhopadhyay et al. |
| 7,196,236 B2 | 3/2007 | Mukhopadhyay et al. |
| 2003/0060670 A1 | 3/2003 | Nair et al. |
| 2004/0119047 A1 | 6/2004 | Singh et al. |
| 2005/0020862 A1 | 1/2005 | Tung et al. |
| 2005/0080302 A1 | 4/2005 | Baker et al. |
| 2005/0090698 A1 | 4/2005 | Merkel et al. |
| 2005/0171391 A1 | 8/2005 | Janssens et al. |
| 2007/0112227 A1 | 5/2007 | Mukhopadhay et al. |
| 2007/0112228 A1 | 5/2007 | Mukhopadhay et al. |
| 2007/0112229 A1 | 5/2007 | Mukhopadhay et al. |
| 2007/0112230 A1 | 5/2007 | Mukhopadhay et al. |
| 2007/0179324 A1 * | 8/2007 | Van Der Puy et al. ....... 570/156 |
| 2007/0238908 A1 * | 10/2007 | Merkel et al. .............. 570/136 |
| 2008/0051610 A1 * | 2/2008 | Wang et al. ............... 570/156 |

FOREIGN PATENT DOCUMENTS

| | | |
|---|---|---|
| EP | 0644173 | 3/1995 |
| EP | 974571 A2 | 1/2000 |
| GB | 844597 | 8/1960 |
| JP | 11140002 | 5/1999 |
| JP | 2000169404 | 6/2000 |
| JP | 2000178543 | 6/2000 |
| WO | 9008752 | 8/1990 |
| WO | 9504021 | 2/1995 |
| WO | 96/01797 A | 1/1996 |
| WO | 98/42645 | 3/1998 |
| WO | 98/21171 | 5/1998 |
| WO | 99/48993 | 9/1999 |
| WO | 00/39242 | 7/2000 |
| WO | 01/07384 | 2/2001 |
| WO | 03027051 | 4/2003 |
| WO | 2005012212 | 2/2005 |
| WO | 2005042451 | 5/2005 |
| WO | 2005108332 | 11/2005 |
| WO | 2005108334 | 11/2005 |
| WO | 2007019355 A | 2/2007 |

OTHER PUBLICATIONS

J Burdon et al. : J Fluorine Chemistry , vol. 40, pp. 283-318, XP002424668.

Banks, et al., Journal of Fluorine Chemistry, vol. 82, Issue 2, pp. 171-174 (1997).

Database WPI Week 199812, AN 1998-126110, XP002427152, Derwent Publications Ltd., London, GB & JP 10 007605A (Central Glass Co Ltd) Jan. 13, 1998 abstract.

Database Beilstein, XP002426121.

Dickson, R.S., Fluorcarbon-Aluminium Compounds, Aust. J. Chem., 1972, 25, 761-8.

Gambareto et al., "The Reaction of chlorine monofloride with unsaturated compounds", 1976, XP00246119.

Henne, Albert L., et al., Chlorinated Derivatives of 2-Floropropane[1] J. American Chemical Society, Jul. 11, 1941: pp. 2692-2694, vol. 63.

Knunyants, I. L. et al. Reaction of Fluoro Olefins, Institute of Heteroorganic Compounds, Bulletin of the Academy of Sciences of USSR, Division of Chemical Sciences—ISSN 0568-5230, p. 1312-1317.

Kunshenko B V et al.: Reaction of Organic Compounds with SF4-HF-Hallogenating System VII, 1992, XP002344564.

March, J. Advanced Organic Chemistry, 1997, pp. 631-636, McGraw-Hill International Book Company, XP002427150.

Vittorio Minanari, A Novel Systensis of Perhalogenated Alkenes, J. Org. Chem. 1992, 57, 5018-5019.

* cited by examiner

METHOD FOR PRODUCING FLUORINATED ORGANIC COMPOUNDS

CROSS-REFERENCES TO RELATED APPLICATIONS

This application is claiming the benefit of U.S. Provisional Application Ser. Nos. 60/763,086, filed Jan. 27, 2006 and 60/733,377, filed Nov. 3, 2005, and is a Continuation-in-Part of U.S. patent application Ser. No. 11/118,503, (pending) filed on Apr. 29, 2005, which in turn claims the priority benefit of U.S. Provisional Patent Application Nos. 60/567,427 and 60/567,425 filed Apr. 16, 2004.

This application is also a Continuation-in-Part of U.S. patent application Ser. No. 11/118,504, filed on Apr. 29, 2005, which in turn claims the priority benefit of U.S. Provisional Patent Application Nos. 60/567,426 and 60/567,429 filed Apr. 16, 2004.

This application is also a Continuation-in-Part of U.S. patent application Ser. No. 11/118,530, (pending) filed on Apr. 29, 2005, which in turn claims the priority benefit of U.S. Provisional Patent Application No. 60/567,428.

The disclosures of each of the above-mentioned applications are incorporated herein by reference. Also incorporated herein by reference are the following U.S. Applications identified by Nos. 60/733,383; 60/733,444; 60/733,355 and 60/733,379, each of which was filed on Nov. 3, 2005. Also incorporated herein by reference, in their entirety, are U.S. Pat. No. 5,986,151.

BACKGROUND OF INVENTION (1) Field of Invention

This invention relates to novel methods for preparing fluorinated organic compounds, and more particularly to methods of producing fluorinated olefins.

(2) Description of Related Art

Hydrofluorocarbons (HFC's), in particular hydrofluoroalkenes such tetrafluoropropenes (including 2,3,3,3-tetrafluoro-1-propene (HFO-1234yf) and 1,3,3,3-tetrafluoro-1-propene (HFO-1234ze)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and thus pose no threat to the ozone layer.

Several methods of preparing hydrofluoroalkanes are known. For example, U.S. Pat. No. 4,900,874 (Ihara et al) describes a method of making fluorine containing olefins by contacting hydrogen gas with fluorinated alcohols. Although this appears to be a relatively high-yield process, for commercial scale production the handling of hydrogen gas at high temperature raises difficult safety related questions. Also, the cost of producing hydrogen gas, such as building an on-site hydrogen plant, can be in many situations prohibitive.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted in this process to unwanted and/or unimportant byproducts, including a sizeable amount of carbon black. The carbon black is not only unwanted, it tends to deactivate the catalyst used in the process.

The preparation of R-1234yf from trifluoroacetylacetone and sulfur tetrafluoride has been described. See Banks, et al., Journal of Fluorine Chemistry, Vol. 82, Iss. 2, p. 171-174 (1997). Also, U.S. Pat. No. 5,162,594 (Krespan) discloses a process wherein tetrafluoroethylene is reacted with another fluorinated ethylene in the liquid phase to produce a polyfluoroolefin product.

SUMMARY OF THE INVENTION

Applicants have developed methods for producing fluorinated organic compounds, including hydrofluoropropenes. In one broad aspect of the present invention, the methods comprise converting a halogenated alkane, and preferably a fluorinated alkane to a fluorinated alkene having an unsaturated terminal carbon with a halogen substituent, and preferably a fluorine substituent. In certain preferred embodiments, the process involves converting at least one compound of formula (I):

$$CF_3[C(R^1_a R^2_b)]_n C(R^3_c R^4_d) \tag{I}$$

to at least one compound of formula (II)

$$CF_3[C(R^1_a R^2_b)]_{n-1} CZ=CHZ \tag{II}$$

where $R^1$, $R^2$, $R^3$ and $R^4$ are each independently a hydrogen atom or a halogen selected from the group consisting of fluorine, chlorine, bromine and iodine, provided that at least one $R^1$, $R^2$, $R^3$ and $R^4$ is a halogen; a and b are independently equal to 0, 1 or 2, provided that (a+b)=2; b and c are independently equal to 0, 1, 2 or 3 and (c+d)=3, n is 1, 2, 3 or 4, and each Z is independently H or a halogen, and when a halogen preferably F, provided that the Z on the terminal carbon is a halogen, and preferably the Z on the terminal carbon is F.

In certain preferred embodiments, each Z is different, and in especially preferred embodiments, each Z is different and the Z on the terminal carbon is F, that is, the compound comprises (HFO-1234ze) for embodiments in which n is 1.

It is also preferred in certain embodiments that the compound of Formula (I) comprises a compound wherein in each of $R^1$ and $R^2$ is H and at least one of $R^3$ or $R^4$ is H. For certain of such embodiments where the compound of Formula I is a three carbon compound, the compound of Formula (IA) is preferred:

$$CF_3CH_2CH_m X_{3-m} \tag{IA}$$

where each X is independently F, Cl, I or Br; and each Z in Formula (II) is independently H or a halogen, and when a halogen, preferably F; and m is 1 or 2. Preferred among the compounds for use in accordance with formula (IA) are pentachloropropane (HCC-240); tetrachlorofluouropropane (HCFC-241); trichlorodifluoropropane (HCFC-242); dichlorotrifluoropropane (HCFC-243); chlorotetrafluoropropane (HCFC-244); and pentafluoropropane (HFC-245), including all isomers of each of these, but preferably HCFC-244fa and HFC-245fa.

The preferred converting step of the present invention comprises catalytically converting the compound of formula (I), more preferably a compound of formula (IA), in either the gas or liquid phase (or a combination of these) to one or more compounds of formula (II). The catalytic conversion step comprises in preferred embodiments introducing said compound of formula (I) to a reaction system under conditions effective to convert, and preferably convert at least about 50%, more preferably at least about 70%, and even more preferably at least about 90%, of said compound of formula (I). It is also generally preferred that said converting step produces a reaction product having at least about 60% selectivity, more preferably at least about 80% selectivity and even more preferably at least about 95% selectivity, to compounds of formula (II), preferably tetrafluoropropene, and even more preferably HFO-1234ze.

DETAILED DESCRIPTION OF PREFERRED EMBODIMENTS

One beneficial aspect of the present invention is that it enables the production of desirable fluroolefins, preferably C3 fluoroolefins, using relatively high conversion and high selectivity reactions. Furthermore, the present methods in certain preferred embodiments permit the production of the desirable fluoroolefins from relatively attractive starting materials. For example, pentafluoropropene, particularly 1,1,3,3,3-pentafluoropropane (HFC-245fa), or chlorotetrafluoroporpane, particularly 1-chloro, 1,3,3,3-tetrafluoropropane (HCFC-244fa) are each compounds of formula (I) that may in certain embodiments be an advantageous starting material. For example, such products may be considered relatively easy to handle, and are generally readily available in commercial quantities or can be easily produced from other readily available materials.

Preferably the formula (I) compound is exposed to reaction conditions effective to produce a reaction product containing one or more of the desired fluorolefins, preferably one or more compounds of formula (II). In one preferred aspect of the present invention, the conversion step comprises a reaction that is sometimes referred to herein for convenience, but not necessarily by way of limitation, as a dehydrohalogenation reaction or more particularly in certain embodiments as a dehydrofluorination reaction. Certain preferred embodiments of the invention are described below, with the headings being used for convenience but not necessarily by way of limitation.

I. Formation of the Compound of Formula II

In certain preferred embodiments, the present converting step is carried out under conditions effective to provide a formula (I) conversion of at least about 40%, more preferably at least about 55%, and even more preferably at least about 70%. In certain preferred embodiments the conversion is at least about 90%, and more preferably about 100%. Further in certain preferred embodiments, the conversion of the compound of formula (I) to produce a compound of formula (II) is conducted under conditions effective to provide a formula (II) selectivity of at least about 85%, more preferably at least about 90%, and more preferably at least about 95%, and even more preferably about 100%.

The preferred reaction step comprised a gas phase reaction (or possibly a combination of gas and liquid phase reactions), and it is contemplated that the reaction can be carried out batch wise, continuous, or a combination of these.

A. Gas Phase Dehydrohalogenation

One highly preferred reaction step in accordance with the present invention may be described by those reactions in which the compound of formula (IB) comprises a compound in which m is 1, that is a compound of formula (IB)

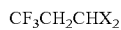  (IB).

For example, one preferred compound of formula (IB) is chlorotetrafluoroporpane, particularly 1-chloro, 1,3,3,3-tetrafluoropropane (244fa). In certain preferred embodiments, the stream containing the compound of formula (I), and preferably (IA) and/or (IB) is preheated to a temperature of from about 150° C. to about 300° C., preferably about 250° C., and introduced into a reaction vessel, which is maintained at the desired temperature, preferably from about 400° C. to about 700° C., more preferably from about 450° C. to about 600° C.

Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, with suitable means to heat the reaction mixture to the desired reaction temperature.

Thus, it is contemplated that the dehydrohalogenation reaction step may be preformed using a wide variety of process parameters and process conditions in view of the overall teachings contained herein. However, it is preferred in certain embodiments that this reaction step comprises a gas phase reaction, preferably in the presence of catalyst.

Although it is contemplated that a wide variety of catalysts and catalyst types may be used in accordance with the present invention, applicants have found that exceptional results can be achieved when the catalyst comprises a charge neutral metal catalyst. As used herein, the term "charge neutral metal catalyst" means a catalyst which includes a metal atom having a substantially neutral charge. For the purpose of convenience, such a charge neutral metal catalyst is designated herein as "M⁰" or "M⁰ catalyst." For catalysts which comprise specific metals, similar designations are used, for example, "Ni⁰ catalyst" to designate a catalyst which contains substantially neutral nickel atoms. In certain preferred embodiments, the present conversion methods comprise providing a carbon- and/or metal-based catalyst, more preferably an M⁰ catalyst (supported or unsupported). Preferably the M⁰ catalyst when used comprises a Ni⁰ catalyst, or a Pd⁰ catalyst, an Fe⁰ catalyst, and combinations of these. In certain preferred embodiments, the catalyst consists essentially of an M⁰ catalyst, preferably an M⁰ catalyst selected from the group consisting of Ni⁰ catalyst, a Pd⁰ catalyst, Fe⁰ catalyst, and combinations of two or more of these. When such catalysts are supported Catellus, is preferred in certain embodiments that the support is carbon and/or activated carbon. It is contemplated, of course, that other catalysts and catalyst supports may be used, including palladium on carbon, palladium-based catalyst (including palladium on aluminum oxides), and it is expected that many other catalysts may be used depending on the requirements of particular embodiments in view of the teachings contained herein. Of course, two or more any of these catalysts, or other catalysts not named here, may be used in combination.

For supported Ni-based catalyst, and even more preferably Ni0-based catalysts (which are preferred in many embodiments including many embodiments in which the formula (I) compound comprises, or consists essentially of, one or more compounds of formula (IA) and/or formula (IB)), it is generally preferred that Ni(I1) acetylacetonate precursor and tetrabutylammonium bromide are first brought together to form the catalyst initially and then are exposed to reduction conditions, for example exposure to hydrogen, to convert the Ni(I1) to Ni(0). It is also generally preferred that catalyst be dried and receive a fluorination treatment before use. One preferred method of forming the preferred catalyst of this type is disclosed in the Examples hereof.

For activated carbon catalysts, which are also preferred in many embodiments including many embodiments in which the formula (I) compound comprises, or consists essentially of, one or more compounds of formula (IA) and/or (IB), it is generally preferred that activated carbon be exposed to drying and fluorination treatment before use. One preferred method of performing forming the preferred catalyst of this type is disclosed in the Examples hereof.

In general it is preferred that the catalysts, and particularly the activated carbon catalysts, are fluorinated, preferably for a period of from about several hours (e.g., 6 hours). In preferred embodiments, fluorination of the catalysts comprises exposing the catalyst to a stream of HF at about reaction temperature and under slight pressure, for example about 35 psia.

The gas phase dehydrohalogenation reaction may be conducted, for example, by introducing a gaseous form of a compound of formula (I), and preferably (IA) into a suitable reaction vessel or reactor. Preferably the vessel is comprised of materials which are resistant to corrosion as Hastelloy, Inconel, Monel and/or fluoropolymers linings. Preferably the vessel contains catalyst, for example a fixed or fluid catalyst bed, packed with a suitable dehydrohalogenation catalyst, preferably as described herein, with suitable means to heat the reaction mixture to the desired reaction temperature.

While it is contemplated that a wide variety of reaction temperatures may be used, depending on relevant factors such as the catalyst being used and the most desired reaction product, it is generally preferred that the reaction temperature for the dehydrohalogentation step, particularly where the formula (I) compound comprises (and even more preferably consists essentially of compounds of formula (IA) and/or (IB)) is from about 400° C. to about 800° C., preferably about 400° C. to about 700° C.

In general it is also contemplated that a wide variety of reaction pressures may be used, depending again on relevant factors such as the specific catalyst being used and the most desired reaction product. The reaction pressure can be, for example, superatmospheric, atmospheric or under vacuum, and in certain preferred embodiments is from about 1 to about 120 psia.

In certain embodiments, an inert diluent gas, such as nitrogen, may be used in combination with the other reactor feed(s). When such a diluent is used, it is generally preferred that the compound of formula (I) comprise from about 50% to greater than 99% by weight based on the combined weight of diluent and formula (I) compound.

It is contemplated that the amount of catalyst use will vary depending on the particular parameters present in each embodiment. In certain preferred embodiments, the contact time is from about 0.1 second to about 1000 second, and preferably from about 3 second to about 50 second.

For embodiments in which the compound of formula (I) comprises or consists essentially of a compound of formula (IB) and/or I(B), and particularly where the desired product of formula (II) is HFO-1234ze, applicants have found that it is preferred to use as the catalyst an $M^0$ cataylast, preferably catalyst comprising substantially neutral palladium, nickel iron and/or carbon, such as a palladium on carbon catalyst or a nickel on carbon catalyst.

Preferably in such dehydrofluorination embodiments as described in this section, the conversion of the formula (I) compound is at least about 50%, more preferably at least about 65%, and even more preferably at least about 90%. Preferably in such embodiments, the selectivity to HFO-1234ze is at least about 70%, more preferably at least about 80% and more preferably at least about 95%.

B. Liquid Phase Reduction

One possible reaction step involves a reaction in which the compound of formula (I), for example 1-chloro, 1,3,3,3 tetrafluoropropane (HCFC-244fa), is contacted with a dehydrohalogenating agent, such as potassium hydroxide (KOH) to form a compound of formula (II). This reaction may be described, by way of illustration but not necessarily by way of limitation, by the following reaction equation:

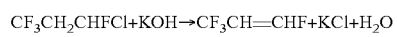

In preferred aspects of such embodiments, a phase transfer agent, such as Crown-18-ether, is included in the reaction mixture, and the KOH is preferably provided as an aqueous solution comprising from about 10% to about 50% by weight KOH, more preferably from about 20% to about 30% by weight.

In certain preferred embodiments, the KOH solution is brought to a relatively cool temperature, preferably from about −10° C. to about 10° C., preferably about 0° C. and introduced into a reaction vessel. The appropriate amount of formula (I) compound, which is preferably from about 0.1 to about 100 mole, preferably, 0.9 to about 10 mole per mole of KOH, is then added to the reaction vessel. The reaction mixture is gradually heated, preferably with the addition of kinetic energy (agitation or stirring) to from about 40° C. to about 80° C., more preferably form about 50° C. to about 60° C. Since the preferred reaction is exothermic, the temperature of the reaction mixture may be allowed to increase to a temperature of from about 60° C. to about 95° C. more preferably form about 65° C. to about 75° C. The reaction pressure in such embodiments may vary, depending on particular processing parameters of each application, but in certain embodiments ranges from about 0 to about 200 psig during the course of the reaction. In certain embodiments the exothermic heat of reaction is removed (such as by cooling) from the reaction mixture so as to maintain the reaction temperature in the range first mentioned above. The overall reaction time in certain preferred embodiments is from about 1 to about 40 hours, more preferably from about 1 to about 10 hours, and even more preferably for about 2 to about 6 hours.

After the designated reaction time, the reaction mixture is preferably cooled to facilitate collection of the reaction product, for example to about 20° C. to about down to 40° C. Preferably, the conversion, and selectivity to HFO-1234ze, are each at least about 70% about 100% and more preferably at least about 90% to about 100%, with a preferred yield of from about 35% to about 95%.

II. Formation of the Compound of Formula I

It is contemplated that a wide variety of sources are known and available for the provision of compounds of formula (I) in accordance with the present invention. For example, in certain embodiments it may be preferred to provide pentachloropropane (HCC-240) and expose this compound to one or more reactions to produce one more compounds in accordance with formula (I). Various other methods for producing compound(s) in accordance with formula (I) are described in U.S. Pat. Nos. 5,710,352; 5,969,198; and 6,023,004, each of which is incorporated herein by reference. Another method, described in U.S. Pat. No. 5,728,904, is said to be economical, amenable to large scale application and uses readily available raw materials. The process of that patent uses three steps, as follows: 1) formation of $CCl_3CH_2CCl_3$ by the reaction of $CCl_4$ with vinylidene chloride; 2) conversion of $CCl_3CH_2CCl_3$ to $CF_3CH_2CF_2Cl$ by reaction with HF in the presence of a fluorination catalyst, selected from $TiCl_4SnCl_4$ or mixtures thereof; and 3) reduction of $CF_3CH_2CF_2Cl$ to $CF_3CH_2CF_2H$. Furthermore, commercial quantities of HFC-245fa, are available from Honeywell International Inc., Morristown, N.J. for use as the starting material of the present process for direct conversion to fluorolefin (for example $CF_3CH=CFH$) by dehydrofluorination according to the process disclosed herein.

EXAMPLES

Additional features of the present invention are provided in the following examples, which should not be construed as limiting the claims in any way.

Examples 1-21

These examples illustrate gas phase dehydrohalogenation of $CF_3CH_2CHF_2$ (HFC-245fa) to $CF_3CH=CHF$ (HFC-1234ze). A 22-inch (½-inch diameter) Monel tube reactor is charged with 50 cc of catalyst, as specified in Table I below. The reactor is mounted inside a heater with three zones (top, middle and bottom). The inlet of the reactor is connected to a pre-heater, which was kept at about 250° C. by electrical heating. Organic (HFC-245fa) is fed from a cylinder kept at 65° C. A flow of inert $N_2$ gas (20 sccm) is maintained throughout. The reactor temperature is brought to the temperature indicated in the table. The HFC-245fa is passed through gas-flow controllers into a pre-heater maintained a temperature of about 250° C. The gas stream coming out of the pre-heater is passed through the catalyst bed at the desired temperature over a specified period of time and at a pressure of from about 2.5-5.3 psig. An on-line GC and a GCMS are used to analyze samples taken at the reactor exit line at regular time intervals. Finally, the reactor effluent is introduced into a 20-60% KOH scrubber solution, and the effluent from the scrubber solution is then condensed to collect the products. The desired product $CF_3CH=CFH$ (HFC-1234ze) is then isolated from the mixture by distillation. The conversion of HFC-245fa is from about 50% to about 100% and the selectivity to HFC-1234ze is from about 60% to about 100%, depending on the reaction conditions. The traces of byproducts obtained were $CHF_3$ and $CH2=CHF$.

The results are shown in Table I below.

TABLE 1

HFC-245fa → $CF_3CH=CFH$ (HFO-1234ze)

| Example#/Catalyst | HFC-245fa, gm/hour | T, ° C. | % Conv. of 245fa | % Selec. to 1234ze |
|---|---|---|---|---|
| Example 1/A | 15 | 495 | 30 | 100 |
| Example 2/A | 15 | 525 | 68 | 100 |
| Example 3/A | 15 | 565 | 100 | 85 |
| Example 4/B | 15 | 515 | 82 | 100 |
| Example 5/C | 15 | 515 | 86 | 100 |
| Example 6/D | 15 | 515 | 91 | 100 |
| Example 7/E | 15 | 515 | 100 | 100 |
| Example 8/F | 15 | 475 | 78 | 45 |
| Example 9/G | 15 | 475 | 82 | 43 |
| Example 10/H | 15 | 475 | 85 | 43 |
| Example 11/I | 15 | 475 | 85 | 44 |
| Example 12/J | 15 | 515 | 68 | 100 |
| Example 13/K | 15 | 515 | 76 | 100 |
| Example 14/L | 15 | 515 | 88 | 98 |
| Example 15/M | 15 | 515 | 100 | 96 |
| Example 16/A | 15 | 515 | 68 | 100 |
| Example 17/AA | 15 | 515 | 76 | 100 |
| Example 18/A | 15 | 515 | 88 | 98 |
| Example 19/AA | 15 | 515 | 100 | 96 |
| Example 20/C | 520 | 96 | 80 | 60 |
| Example 21/G | 500 | 63 | 100 | 73 |

Catalysts (100 cc):
A is activated carbon;
AA is activated carbon - acid treated;
B is 0.2 wt % Ni/C;
C is 0.8 wt % Ni/C;
D is 1.1 wt % Ni/C;
E is 1.8 wt % Ni/C;
F is 0.4 wt % Ni/$Cr_2O_3$;
G is 0.6 wt % Ni/$Cr_2O_3$;
H is 0.7 wt % Ni/$Cr_2O_3$;
I is 1 wt % Ni/$Cr_2O_3$;
J is 0.4 wt % Ni/$Al_2O_3$;
K is 0.6 wt % wt % Ni/$Al_2O_3$;
L is 0.7 wt % wt % Ni/$Al_2O_3$;
M is 1 wt % wt % Ni/$Al_2O_3$;
the product, 1234ze is obtained as a cis-1234ze (2-5 mol %) and trans-1234ze (95-98 mol %) mixture.

Examples 22-24

These examples illustrate gas phase dehydrohalogenation of $CF_3CH_2CHFCl$ (HCFC-244fa) to $CF_3CH=CHF$ (HFO-1234ze). The procedure of Examples 1-21 is repeated except HCFC-244fa is used in place of HFC-245fa. The traces of byproducts (less than 0.5% combined) identified in GC/MS were CF3Cl and CF3CH2Cl.

The results are shown in Table 2 below.

TABLE 1

HFC-244fa → $CF_3CH=CFH$ (HFO-1234ze)

| Example#/Catalyst | HFC-244fa, gm/hour | T, ° C. | % Conv. of 244fa | % Selec. to 1234ze |
|---|---|---|---|---|
| Example 19/AA | 15 | 515 | 100 | 96 |
| Example 20/C | 520 | 96 | 80 | 60 |

TABLE 1-continued

HFC-244fa → CF₃CH=CFH (HFO-1234ze)

| Example#/ Catalyst | HFC-244fa, gm/hour | T, ° C. | % Conv. of 244fa | % Selec. to 1234ze |
|---|---|---|---|---|
| Example 21/G | 500 | 63 | 100 | 73 |

Catalysts - as defined in Table 1:
A is activated carbon;
AA is activated carbon - acid treated;
B is 0.2 wt % Ni/C;
C is 0.8 wt % Ni/C;
D is 1.1 wt % Ni/C;
E is 1.8 wt % Ni/C;
F is 0.4 wt % Ni/Cr₂O₃;
G is 0.6 wt % Ni/Cr₂O₃;
H is 0.7 wt % Ni/Cr₂O₃;
I is 1 wt % Ni/Cr₂O₃;
J is 0.4 wt % Ni/Al₂O₃;
K is 0.6 wt % wt % Ni/Al₂O₃;
L is 0.7 wt % wt % Ni/Al₂O₃;
M is 1 wt % wt % Ni/Al₂O₃;

Examples 25

This example illustrates the liquid phase dehydrochlorination of CF₃CH₂CHFCl (HCFC-244fa) to CF₃CH=CHF (HFO-1234ze). About 150 g of 20% KOH solution, 1 g of 18-Crown ether, and 10 g of CF₃CHClCH₂F are charged to a teflon-lined 300 ml autoclave. The mixture is stirred at 50° C. for 6 hours. The reaction progress is monitored by collecting samples and analyzing them by GC and MS in every 30 min. After the stipulated reaction period, the overhead gas mixture was transferred to a collection cylinder at −70° C. Analysis and overall material balance confirms a yield of 55%.

Having thus described a few particular embodiments of the invention, various alterations, modifications, and improvements will readily occur to those skilled in the art. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method of preparing fluorinated organic compounds comprising converting a compound having a first formula $$CF_3CH_2CHFCl$$

to a compound having a second formula $$CF_3CH=CHF$$

wherein said converting involves a vapor phase contacting of said compound of the first formula with at least one neutral charge metal catalyst; and
wherein the neutral charge metal catalyst is selected from the group consisting of Ni⁰, Pd⁰, Fe⁰ catalysts, and combinations of two or more of these.

2. The method of claim 1 wherein said converting step is carried out under conditions effective to provide a conversion of at least one compound according to the first formula of at least about 40%.

3. The method of claim 1 wherein said converting step is carried out under conditions effective to provide a conversion of at least one compound according to the first formula of at least about 80%.

4. The method of claim 1 wherein said converting step is carried out under conditions effective to provide a conversion of at least one compound according to the first formula of at least about 90%.

5. The method of claim 1 wherein said converting step is carried out under conditions effective to provide a selectivity to at least one compound according to the second formula of at least about 95%.

6. The method of claim 1 wherein said converting step is carried out under conditions effective to provide a selectivity to at least one compound according to the second formula of at least about 90%.

7. A method of preparing fluorinated organic compounds comprising the dehydrochlorination of a compound of formula (I)

$$CF_3[C(R^1_aR^2_b)]_nC(R^3_cR^4_d) \quad (I)$$

to at least one compound of formula (II)

$$CF_3[C(R^1_aR^2_b)]_{n-1}CZ=CHZ \quad (II)$$

where
R, R², R³ and R⁴ are each independently a hydrogen atom or a halogen selected from the group consisting of fluorine, chlorine, bromine and iodine, provided that at least one R¹, R², R³ and R⁴ is chlorine and the compound has hydrogen on the last two carbons;
a and b are independently equal to 0, 1 or 2, provided that (a+b)=2;
c and d are independently equal to 0, 1, 2 or 3, provided that (c+d)=3;
n is 1, 2, 3 or 4, and
each Z is independently H or a halogen, further provided that the Z on the terminal carbon is a halogen;
wherein said converting step comprises catalytically converting the compound of formula (I) to one or more compounds of formula (II) by exposing the compound of formula (I) to a neutral charge metal catalyst; and
wherein the neutral charge metal catalyst is selected from the group consisting of Ni⁰, Pd⁰, Fe⁰ catalysts, and combinations of two or more of these.

8. The method of claim 7 wherein said converting step is carried out under conditions effective to provide a conversion of at least one compound according to formula (I) of at least about 40%.

9. The method of claim 7 wherein said converting step is carried out under conditions effective to provide a conversion of at least one compound according to formula (I) of at least about 80%.

10. The method of claim 7 wherein said converting step is carried out under conditions effective to provide a conversion of at least one compound according to formula (I) of at least about 90%.

11. The method of claim 7 wherein said converting step is carried out under conditions effective to provide a formula (II) selectivity of at least about 95%.

12. The method of claim 7 wherein said converting step is carried out under conditions effective to provide selectivity to at least one compound according to formula (11) of at least about 90%.

13. The method of claim 7 wherein the Z on the terminal carbon is a fluorine.

14. The method of claim 13 wherein n is 1.

15. The method of claim 14 wherein the compound of formula (II) comprises HFO-1234ze.

16. The method of claim 7 wherein the compound of formula (I) is selected from the group consisting of:
dichlorotrifluoropropane (HCFC-243);

chlorotetrafluoropropane (HCFC-244); and all isomers and combinations of each of these.

17. The method of claim 7 wherein the compound of formula (I) comprises HCFC-244fa.

18. The method of claim 7 wherein the neutral charge metal catalyst comprises a $Ni^0$ catalyst.

19. The method of claim 18 wherein the neutral charge metal catalyst comprises Ni on carbon.

20. The method of claim 18 wherein the neutral charge metal catalyst comprises Ni on chromium oxide.

21. The method of claim 1 wherein the neutral charge metal catalyst comprises a $Ni^0$ catalyst.

22. The method of claim 21 wherein the neutral charge metal catalyst comprises Ni on carbon.

23. The method of claim 21 wherein the neutral charge metal catalyst comprises Ni on chromium oxide.

* * * * *